United States Patent
Song et al.

(10) Patent No.: US 11,406,848 B2
(45) Date of Patent: Aug. 9, 2022

(54) ULTRASONIC THERAPY DEVICE USING HIFU AND CONTROL METHOD THEREOF

(71) Applicant: SOGANG UNIVERSITY RESEARCH FOUNDATION, Seoul (KR)

(72) Inventors: Tai-Kyong Song, Seoul (KR); Pilsu Kim, Seoul (KR); Jiwon Park, Seoul (KR); Sua Bae, Seoul (KR)

(73) Assignee: SOGANG UNIVERSITY RESEARCH FOUNDATION, Seoul (KR)

( * ) Notice: Subject to any disclaimer, the term of this patent is extended or adjusted under 35 U.S.C. 154(b) by 570 days.

(21) Appl. No.: 16/313,654

(22) PCT Filed: Jun. 28, 2016

(86) PCT No.: PCT/KR2016/006903
§ 371 (c)(1),
(2) Date: Dec. 27, 2018

(87) PCT Pub. No.: WO2018/004026
PCT Pub. Date: Jan. 4, 2018

(65) Prior Publication Data
US 2019/0314646 A1  Oct. 17, 2019

(51) Int. Cl.
*A61N 7/02* (2006.01)
*A61N 7/00* (2006.01)

(52) U.S. Cl.
CPC ........ *A61N 7/02* (2013.01); *A61N 2007/0078* (2013.01)

(58) Field of Classification Search
CPC .... A61N 7/02; A61N 7/00; A61N 2007/0078; A61N 2007/0095
See application file for complete search history.

(56) References Cited

U.S. PATENT DOCUMENTS

| 6,613,004 B1 | 9/2003 | Vitek et al. |
| 7,806,839 B2 | 10/2010 | Mast et al. |

(Continued)

FOREIGN PATENT DOCUMENTS

| EP | 2 332 614 | 6/2011 |
| EP | 3 100 767 | 12/2016 |

(Continued)

OTHER PUBLICATIONS

V. D. Agrawal, "Grating-lobe suppression in phased arrays by subarray rotation," in Proceedings of the IEEE, vol. 66, No. 3, pp. 347-349, Mar. 1978, doi: 10.1109/PROC.1978.10904. (Year: 1978).*

(Continued)

*Primary Examiner* — Peter Luong
(74) *Attorney, Agent, or Firm* — Duane Morris LLP; Gregory M. Lefkowitz

(57) ABSTRACT

The present disclosure relates to an ultrasound therapy device using high-intensity focused ultrasound (HIFU) and a control method thereof. The ultrasound therapy device comprises: an array type HIFU converter having a plurality of HIFU conversion elements; and a control unit for performing a control to treat tissues in a focusing area by selecting and driving some of the HIFU conversion elements of the array type HIFU converter and irradiating ultrasound signals to an object through the driven active conversion elements to generate heat energy, wherein, after an elapse of a predetermined time period, the control unit drives a combination of other conversion elements as new active conversion elements in replacement of the active conversion elements.

8 Claims, 9 Drawing Sheets

(56) References Cited

U.S. PATENT DOCUMENTS 8,608,672 B2 * 12/2013 Vortman .............. G10K 11/346
601/2
2013/0060170 A1 * 3/2013 Lee ...................... A61B 8/4494
601/3

FOREIGN PATENT DOCUMENTS

| KR | 1020130026327 | 3/2013 |
|----|---------------|--------|
| KR | 1013555320000 | 1/2014 |
| KR | 1015471430000 | 8/2015 |
| WO | 2015/115683   | 8/2015 |

OTHER PUBLICATIONS

Dupenloup et al., "Reduction of the Grating Lobes of Annular Arrays Used in Focused Ultrasound Surgery", IEEE Transactions on Ultrasonics, Ferroelectris, and Frequency Control, vol. 43, No. 6, Nov. 1996, pp. 991-998.

Hand et al., "A randon phased array device for delivery of high intensity focused ultrasound", Physics in Medicine and Biology, 54 (2009), pp. 5675-5693.

* cited by examiner

ULTRASONIC THERAPY DEVICE USING HIFU AND CONTROL METHOD THEREOF

TECHNICAL FIELD

The present disclosure relates to ultrasound technology for noninvasive treatment, and more particularly, to an ultrasound therapy device for controlling an ultrasonic converter assembly for performing treatment using high intensity focused ultrasound (HIFU) and a method for controlling a plurality of ultrasonic converters provided in the ultrasound therapy device.

BACKGROUND ART

It is known that human body tissues are necrotized when the temperature of the part is 60-85° C. Using this phenomenon, high intensity focused ultrasound (HIFU) treatment is the scheme of focusing ultrasound energy on one point (focal point) to necrotize the lesion tissue by heat (thermal coagulation) and mechanical energy (cavitation). With the development of ultrasound treatment, a specific ultrasound treatment, especially, HIFU, is applied to damaging dose to effectively treat many types of diseases, especially tumors. When comparing to the conventional surgery and chemotherapy, HIFU treatment causes less damage to patients and achieves non-invasive treatment. Accordingly, the clinical applications of HIFU are developed fast. The symptoms include liver cancer, bone sarcoma, breast cancer, pancreas cancer, kidney cancer, soft tissue tumor and pelvic tumor.

In general, an ultrasound tumor treatment device employs sphere focusing. Ultrasound emitted from all points is focused on the center of a sphere. The emitter on the ultrasound treatment device emits ultrasound from the outside of the body to the inside of the body, and the ultrasound is focused to form a high energy focal point during emission and transmission. Accordingly, high intensity and continuous ultrasound energy is applied to the patient's lesion region.

The effect of too high temperature (65-100° C.), the cavitation effect, the mechanical effect and the sonochemical effect generated from the focal point are used to selectively cause coagulative necrosis of the affected tissue, and prevent the proliferation, invasion and metastasis of tumor.

The accurate, safe and effective localization of the focal point is essential for successful treatment while applying HIFU treatment, and there is a need to further improve the convenience of operation for positioning the target. Accordingly, in performing treatment through HIFU signals without damaging the important vessels and organs, most of all, it is required to identify an area under influence of HIFU signals and accurately know the influence on an area to be treated and other normal tissues.

The related literature presented below introduces the structure of a converter (transducer) that can reduce the size of the grating lobe in implementing high intensity focused ultrasound.

RELATED LITERATURE

Korean Patent Publication No. 10-2013-0055972, published May 29, 2013

DISCLOSURE

Technical Problem

The technical problem to be solved by the embodiments of the present disclosure is, when necrotizing the lesion through high intensity focused ultrasound treatment, to minimize the generation of the grating lobe by beam focusing on an area that is not intended by an operator, and solve the problem with ultrasound therapy efficiency reduction caused by ultrasonic irradiation damage accumulated in normal tissues while long-term treatment continues.

Technical Solution

To solve the above-described technical problem, an ultrasound therapy device adopting an electrical control scheme according to an embodiment of the present disclosure includes an array type high intensity focused ultrasound (HIFU) converter having a plurality of HIFU conversion elements, and a control unit which performs control to treat tissues in a focusing area by selecting and driving some of the conversion elements of the array type HIFU converter and irradiating ultrasound signals to an object through the driven active conversion elements to generate heat energy, and after an elapse of a predetermined time period, the control unit drives conversion elements selected for a different combination of conversion elements as new active conversion elements in replacement of the active conversion elements.

In the ultrasound therapy device adopting an electrical control scheme according to an embodiment, the control unit changes a combination of conversion elements that constitute active conversion elements over time, and performs control such that beam focusing through the conversion elements included in the combination before the change and beam focusing through the conversion elements included in the combination after the change have a same location of main lobe and different locations of grating lobe. Additionally, the ultrasound therapy device may further include a storage unit which generates and pre-stores a plurality of combinations of conversion elements having a same location of main lobe and different locations of grating lobe, and the control unit may read the combinations of conversion elements stored in the storage unit in a sequential order, and make replacement and drive as active conversion elements at a predetermined time interval.

In the ultrasound therapy device adopting an electrical control scheme according to an embodiment, the control unit may change a combination of conversion elements that constitute active conversion elements for varying distances between conversion elements from a center of the array type HIFU converter over time.

In the ultrasound therapy device adopting an electrical control scheme according to an embodiment, the active conversion elements may be selected from conversion elements arranged randomly on the array type HIFU converter, or arranged forming a sparse array, a Fermat's spiral or a concentric ring, or arranged symmetrically with respect to one reference axis.

To solve the above-described technical problem, an ultrasound therapy method adopting an electrical control scheme according to an embodiment of the present disclosure includes (a) selecting and driving some conversion elements from an array type HIFU converter having a plurality of HIFU conversion elements, (b) treating tissues in a focusing area by irradiating ultrasound signals to an object through the driven active conversion elements to generate heat energy, (c) after an elapse of a predetermined time period, selecting conversion elements for a different combination of conversion elements and driving as new active conversion elements in replacement of the active conversion elements, and (d) treating the tissues in the focusing area using the driven new active conversion elements.

In the ultrasound therapy method adopting an electrical control scheme according to an embodiment, the step (c) includes selecting new active conversion elements by changing a combination of conversion elements that constitute active conversion elements, and stopping the operation of the existing active conversion elements, and driving the new active conversion elements, and performing control such that beam focusing through the conversion elements included in the combination before the change and beam focusing through the conversion elements included in the combination after the change have a same location of main lobe and different locations of grating lobe. Additionally, the ultrasound therapy method may further include generating and pre-storing a plurality of combinations of conversion elements having a same location of main lobe and different locations of grating lobe, and the step (c) may include reading the pre-stored combinations of conversion elements in a sequential order and making replacement and driving as active conversion elements at a predetermined time interval.

In the ultrasound therapy method adopting an electrical control scheme according to an embodiment, the step (c) may include changing a combination of conversion elements that constitute active conversion elements for varying distances between conversion elements from a center of the array type HIFU converter over time.

In the ultrasound therapy method adopting an electrical control scheme according to an embodiment, the active conversion elements selected through the step (a) and the step (c) may be selected from conversion elements arranged randomly on the array type HIFU converter, or arranged forming a sparse array, a Fermat's spiral or a concentric ring, or arranged symmetrically with respect to one reference axis.

To solve the above-described technical problem, an ultrasound therapy device adopting a mechanical control scheme according to another embodiment of the present disclosure includes an array type HIFU converter having a plurality of HIFU conversion elements, a control unit which performs control to treat tissues in a focusing area by driving the conversion elements of the array type HIFU converter and irradiating ultrasound signals to an object to generate heat energy, and a rotation unit which rotates the array type HIFU converter while maintaining a plane facing the object.

In the ultrasound therapy device adopting a mechanical control scheme according to another embodiment, the rotation unit may rotate the array type HIFU converter around a center of the array type HIFU converter to continuously change a location of grating lobe over time.

In the ultrasound therapy device adopting a mechanical control scheme according to another embodiment, when the focusing area formed by beam focusing is disposed on a rotation axis of the rotation unit, the control unit may fix a location of main lobe to the object to be treated without change in beam focusing signal irrespective of rotation of the array type HIFU converter.

In the ultrasound therapy device adopting a mechanical control scheme according to another embodiment, when the focusing area formed by beam focusing is not disposed on a rotation axis of the rotation unit, the control unit may control the beam focusing signals of each of the conversion elements of the array type HIFU converter such that a main lobe changing in focusing position with the rotation of the array type HIFU converter is disposed in the object to be treated.

In the ultrasound therapy device adopting a mechanical control scheme according to another embodiment, the conversion elements may be arranged randomly on the array type HIFU converter, or arranged forming a sparse array, a Fermat's spiral or a concentric ring, or arranged symmetrically with respect to one reference axis.

In the ultrasound therapy device adopting a mechanical control scheme according to another embodiment, the control unit may drive all or some of the conversion elements of the array type HIFU converter, and perform control such that when some conversion elements are driven, the focusing area formed by beam focusing implemented by the driven conversion elements is disposed on the rotation axis of the rotation unit.

To solve the above-described technical problem, an ultrasound therapy method adopting a mechanical control scheme according to another embodiment of the present disclosure includes (a) treating tissues in a focusing area by driving conversion elements of an array type HIFU converter having a plurality of high intensity focused ultrasound (HIFU) conversion elements and irradiating ultrasound signals to an object to generate heat energy, and (b) rotating the array type HIFU converter while maintaining a plane facing the object to continuously change a location of grating lobe over time.

In the ultrasound therapy method adopting a mechanical control scheme according to another embodiment, when the focusing area formed by beam focusing is disposed on a rotation axis of the rotation unit, the step (b) may include fixing a location of main lobe to the object to be treated without change in beam focusing signal irrespective of rotation of the array type HIFU converter.

In the ultrasound therapy method adopting a mechanical control scheme according to another embodiment, when the focusing area formed by beam focusing is not disposed on a rotation axis of the rotation unit, the step (b) may include controlling the beam focusing signals of each of the conversion elements of the array type HIFU converter such that a main lobe changing in focusing position with the rotation of the array type HIFU converter is disposed in the object to be treated.

In the ultrasound therapy method adopting a mechanical control scheme according to another embodiment, when some of the conversion elements are driven through the step (a), the step (b) may include performing control such that the focusing area formed by beam focusing implemented by the driven conversion elements is disposed on a rotation axis of the rotation unit.

Advantageous Effects

The embodiments of the present disclosure continuously changes the location of the grating lobe while fixing the location of the main lobe, thereby suppressing the side effects of ultrasound focused on an unintended area by the grating lobe and damage of normal tissues, mitigating pain in patients during treatment, reducing the risk for burns to skin in contact with the converter as well as the cooling time of the converter, and enabling efficient ultrasound therapy.

DETAILED DESCRIPTION OF MAIN ELEMENTS

Figure 1:
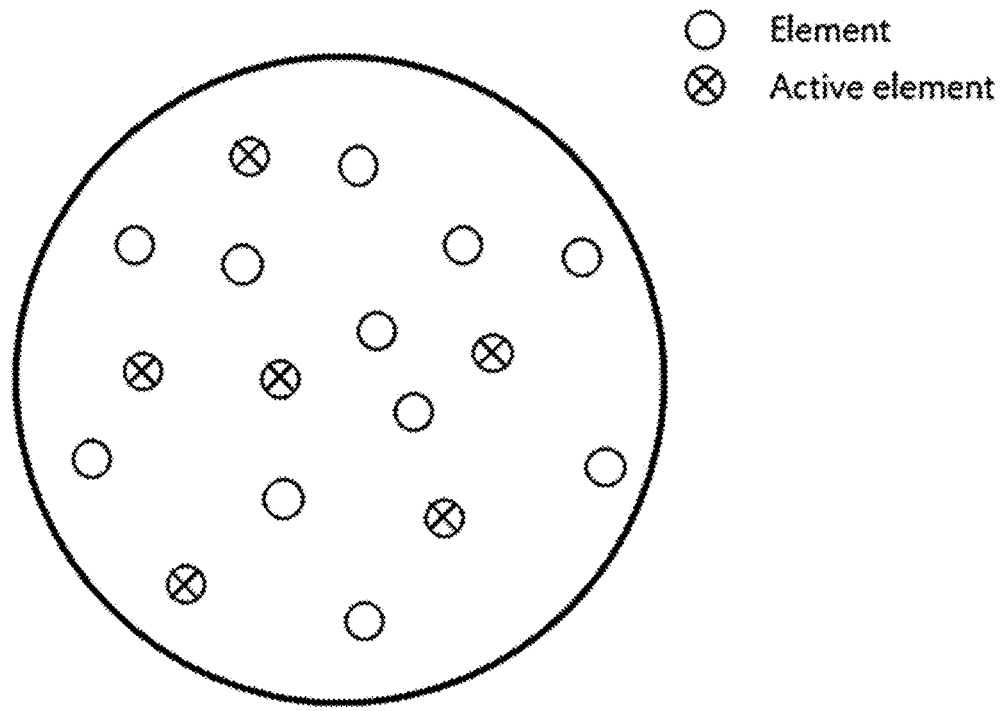
FIG. 1 is a diagram showing a high intensity focused ultrasound (HIFU) converter structure implemented with a sparse array structure.

10: Array type HIFU converter
13, 15: Combination of active conversion elements
30: Control unit
40: Storage unit
50: Rotation unit

BEST MODE

An ultrasound therapy device according to an embodiment of the present disclosure includes: an array type high intensity focused ultrasound (HIFU) converter having a plurality of HIFU conversion elements; and a control unit to perform control to treat tissues in a focusing area by selecting and driving some of the conversion elements of the array type HIFU converter and irradiating ultrasound signals to an object through the driven active conversion elements to generate heat energy, wherein, after an elapse of a predetermined time period, the control unit drives conversion elements selected for a different combination of conversion elements as new active conversion elements in replacement of the active conversion elements.

MODE FOR INVENTION

Prior to a detailed description of the embodiments of the present disclosure, after a brief introduction to the physical features of ultrasound therapy technology based on high intensity focused ultrasound, the technical means adopted by the embodiments of the present disclosure to overcome the practical problems and limitations pointed out in medical places will be suggested.

High intensity focused ultrasound (HIFU) is noninvasive treatment technology that irradiates high intensity of ultrasound into human body tissues to necrotize lesion tissues such as cancers in the human body tissue, and after converting electrical signals to ultrasound signals using a plurality of converters arranged in a probe, irradiates the ultrasound signals into the human body. In general, HIFU focuses higher intensity of ultrasound signals than those used for ultrasound imaging on an area to be treated and irradiates a few times to necrotize the lesion tissues. The irradiated energy is converted to heat energy and heats the tissues disposed in the focusing area of ultrasound to high temperature into coagulative necrosis. In this instance, the HIFU converter used in treatment is made by attaching a few tens or hundreds of ultrasonic conversion elements in the shape of a circular or polygonal plate to a concave frame with the radius that is equal to the focal length. This converter is a so-called array type converter, and the array type converter may bring about a spot on which unintended ultrasonic energy is focused in an area other than the focal point according to the location and shape of the conversion elements. Emission in an unintended area is known as grating lobe, which may cause local heating in an unintended area during HIFU treatment. The heating by the grating lobe is one of side effects frequently occurring during HIFU treatment, and causes a serious problem such as pain or necrosis of normal tissues. On the other hand, in transmitting and receiving ultrasound waves using the array type converter, the wider the steering angle, the greater the influence of the grating lobe. Accordingly, in the HIFU treatment, the electrical steering range of ultrasound is limited to avoid the influence of the grating lobe, and after all, the physical movements of the converter are needed, and there are problems with longer treatment time and lower treatment efficiency. Additionally, to prevent the necrosis of normal tissues by heat generated in an unintended area due to the influence of the grating lobe, a cooling process is performed during treatment, which also causes the problems with longer treatment time and lower treatment efficiency.

Figure 2:
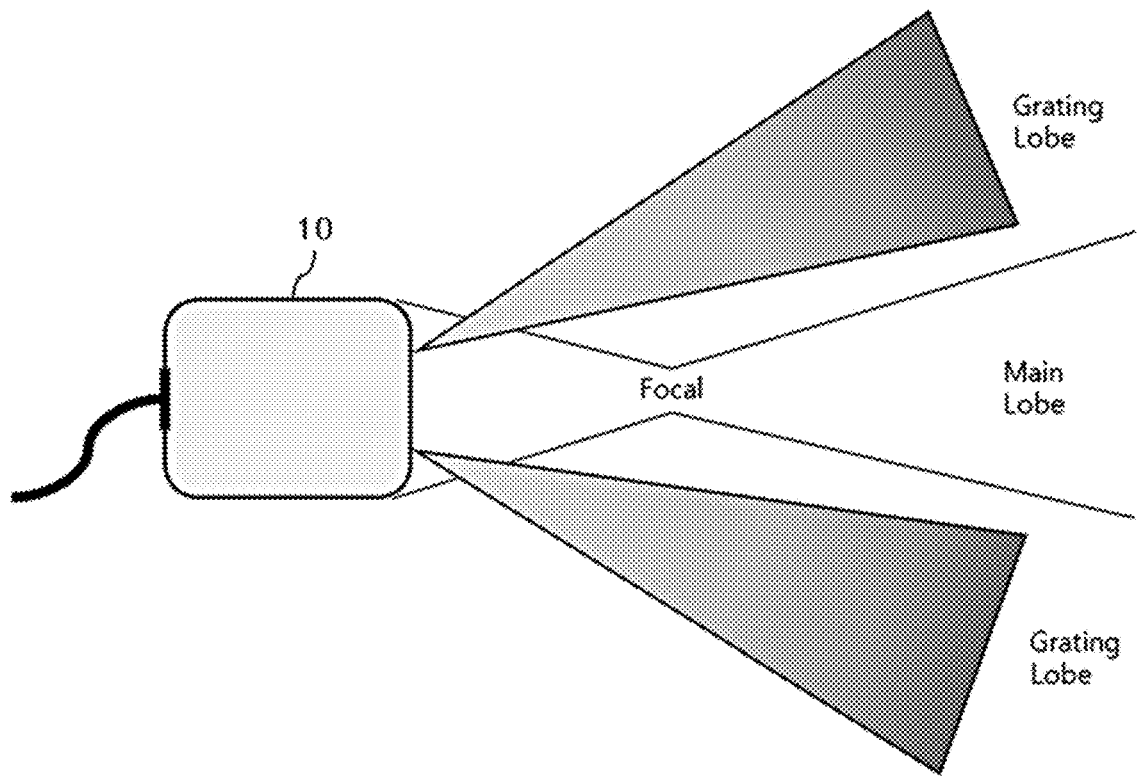
FIG. 2 is an exemplary diagram showing a beam pattern generated by an HIFU converter adopting an array structure such as a sparse array scheme.

To minimize this problem of the grating lobe, many studies have been made on an ultrasonic converter having conversion elements arranged according to a random method or a sparse array scheme. FIG. 1 is a diagram showing an HIFU converter structure implemented with a sparse array structure, and these methods can reduce the size of the grating lobe, but rather they are confronted by a side effect that the grating lobe is generated over a wider area. FIG. 2 is an exemplary diagram showing a beam pattern generated by an HIFU converter adopting an array structure such as a sparse array scheme, and referring to FIG. 2, it shows the location of grating lobe formed in an unintended area other than the main lobe where substantial treatment is performed with respect to a focal point of a beam formed from the HIFU converter 10.

In addition, when long-term treatment is performed using the array type HIFU converter, because the location of the grating lobe is fixed, the radiated ultrasound is accumulated with the passage of time, and eventually the same result is obtained such as damage to the area where the grating lobe is disposed. That is, the problem with damage of normal tissues in the parts other than the area to be treated through long-term treatment occurs similarly.

Accordingly, in necrotizing the lesion with high intensity focused ultrasound treatment, the embodiments of the present disclosure presented below adopt a control scheme that maintains focusing of ultrasound on a focusing area, and can minimize the grating lobe resulting from beam focusing in an unintended area, to minimize damage of normal tissues and increase the treatment efficiency.

To this end, the embodiments of the present disclosure controls the ultrasonic irradiation method to fix the location of the main lobe to the focusing area, and continuously change the location of the grating lobe during treatment, so as to reduce the size of the grating lobe that is accumulated while treatment continues. The substantial control method may be largely classified into an electrical control scheme and a mechanical control scheme. Hereinafter, the embodiments of the present disclosure will be described in detail with reference to the accompanying drawings. The same reference numerals indicated in the drawings denote the same elements.

(1) Electrical Control Scheme

Figure 3:
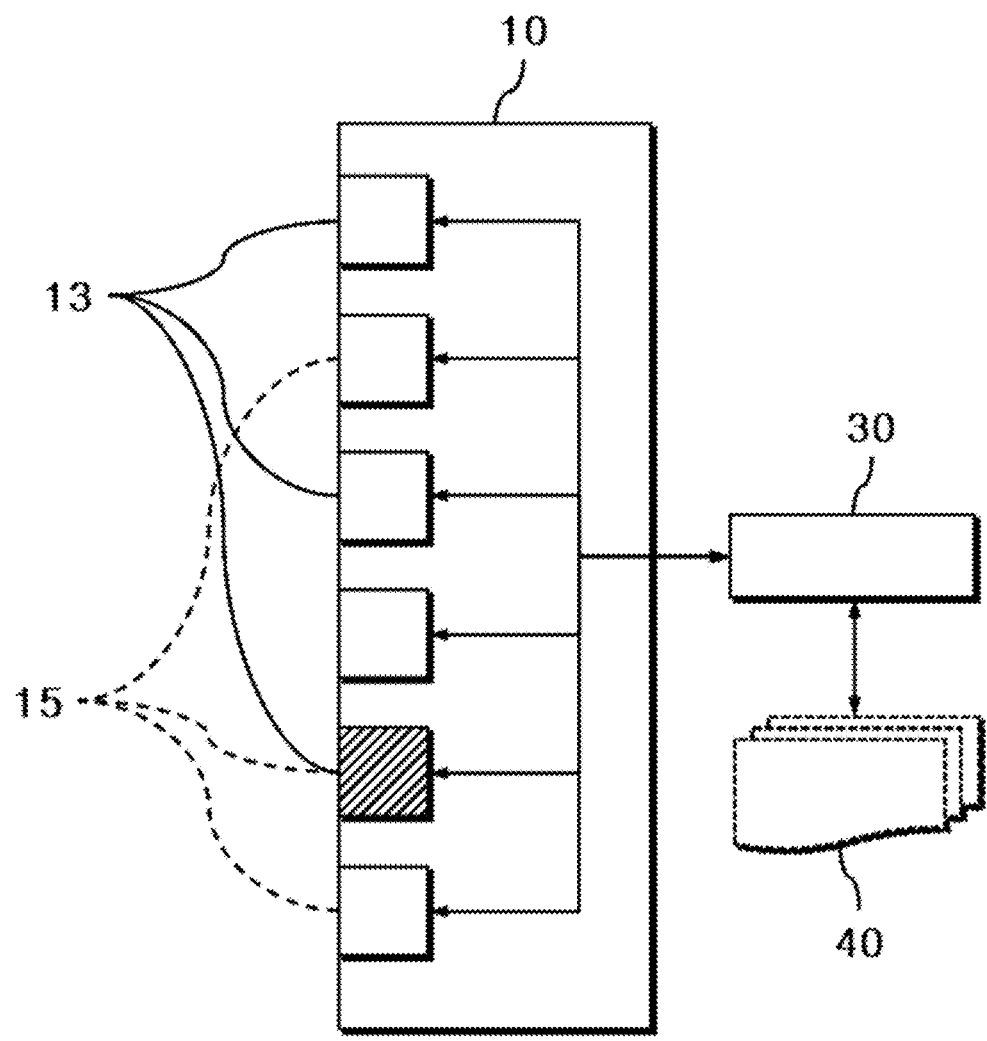
FIG. 3 is a block diagram showing an ultrasound therapy device adopting an electrical control scheme that changes the location of the grating lobe according to an embodiment of the present disclosure.

FIG. 3 is a block diagram showing the ultrasound therapy device adopting the electrical control scheme that changes the location of the grating lobe according to an embodiment of the present disclosure.

The array type HIFU converter 10 has a plurality of HIFU conversion elements, and has a structure in which a larger number of conversion elements than active ultrasonic conversion elements (active elements) operating at one point is arranged on a frame regularly or irregularly. That is, instead of simultaneously driving all the conversion elements of the array type HIFU converter 10, some of them are driven and used for beam focusing.

Referring to FIG. 3, it exemplarily shows that active conversion elements 13 of a first group selected three conversion elements, and active conversion elements 15 of a second group selected a combination of three other conversion elements. In this instance, the first group and the second group are driven at different points in time, and a combination of conversion elements included in each group are only different and each of all the individual conversion elements does not need to be arranged in a non-overlapping manner. In FIG. 3, one conversion element (indicated by slashed lines) in the first group 13 and the second group 15 is included in common.

Meanwhile, the active conversion elements driven at one point in time may be selected from conversion elements arranged randomly on the array type HIFU converter, or arranged forming a sparse array, a Fermat's spiral or a concentric ring, or arranged symmetrically with respect to one reference axis (i.e., arranged counter-randomly).

A control unit 30 performs control to treat tissues in a focusing area by selecting and driving some of the conversion elements of the array type HIFU converter 10 and irradiating ultrasound signals to an object through the driven active conversion elements to generate heat energy. Additionally, after an elapse of a predetermined time period, the control unit 30 drives conversion elements selected for a different combination of conversion elements as new active conversion elements in replacement of the active conversion elements. This control method is designed with an aim of continuously changing the location of the grating lobe while fixing the location of the main lobe to the focusing area in the beam focusing process for ultrasound therapy.

To this end, the control unit 30 changes the combination of conversion elements that constitute the active conversion elements over time, and controls each conversion element such that beam focusing through the conversion elements included in the combination before the change and beam focusing through the conversion elements included in the combination after the change have the same location of the main lobe and different locations of the grating lobe. That is, the formation location of the grating lobe is changed by changing the combination of active conversion elements to minimize damage accumulated by the grating lobe, not the main lobe, while treatment continues.

Meanwhile, the ultrasound therapy device of FIG. 3 may further include a storage unit 40 to generate and pre-store a plurality of preset combinations of conversion elements having the same location of the main lobe and different locations of the grating lobe. In this case, the control unit 30 may read the combinations of conversion elements stored in the storage unit 40 in a sequential order, and replace and drive as active conversion elements at a predetermined time interval.

Figure 4:
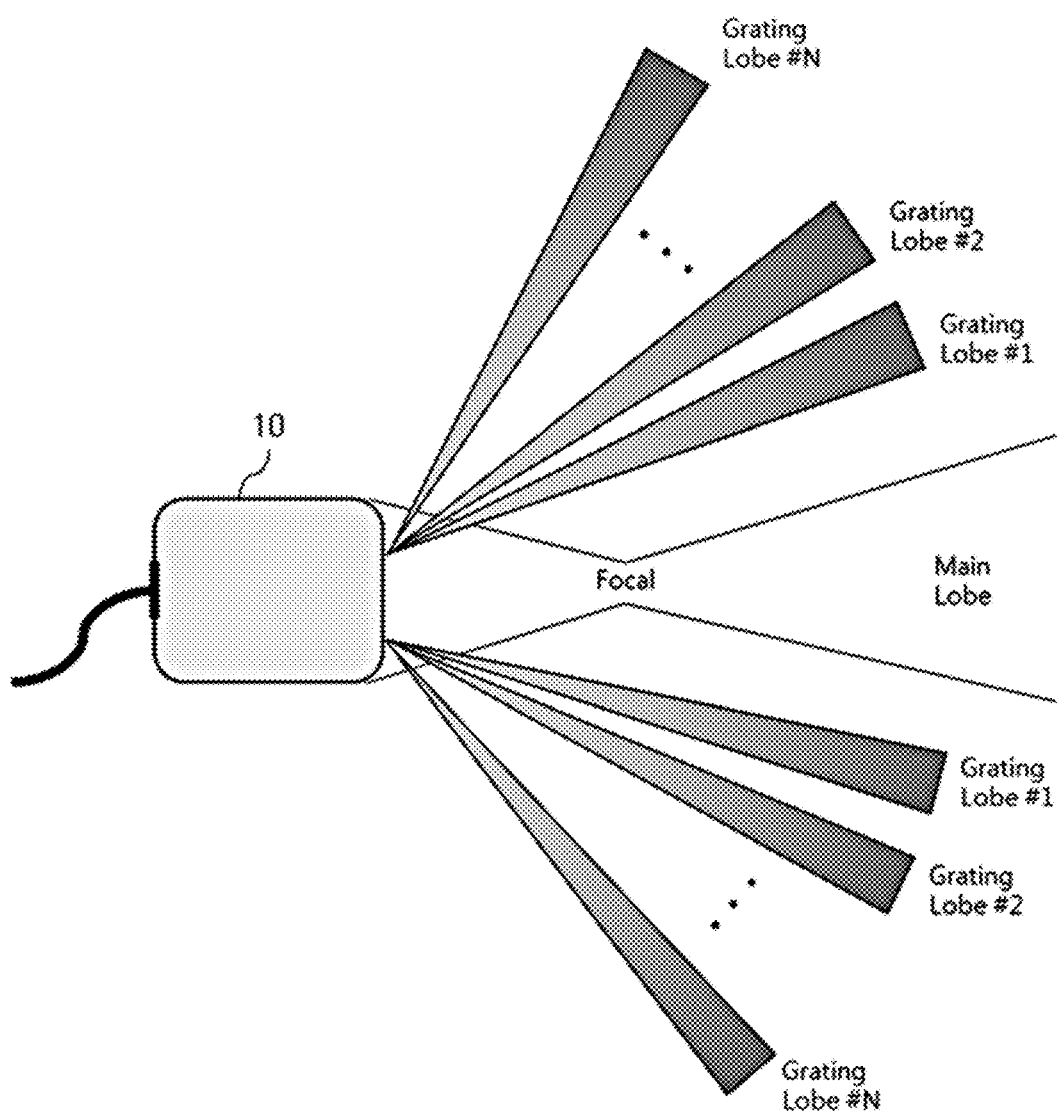
FIG. 4 is an exemplary diagram showing a beam pattern generated through the ultrasound therapy device of FIG. 3 according to an embodiment of the present disclosure.

FIG. 4 is an exemplary diagram showing a beam pattern generated through the ultrasound therapy device of FIG. 3 according to an embodiment of the present disclosure. Referring to FIG. 4, it is assumed that a plurality of combinations of active conversion elements is provided, and as time goes by, they are replaced and driven, and it shows that by this change of the active conversion elements, the location of the main lobe is fixed, but the location of the grating lobe continuously changes. Through this control method, damage accumulation caused by the continuous operation of the grating lobe can be prevented.

Generally, a beam pattern of a point on which ultrasound is focused according to the azimuth and depth is the same as the following Equation 1:

$$\left[ D \cdot \mathrm{sinc}\left(\frac{x}{R_0 \lambda} - \frac{\sin\psi}{\lambda}\right) \cdot D * \sum_{k=-\infty}^{\infty} \frac{1}{d_k} \delta\left(\frac{x}{R_0 \lambda} - \frac{1}{d_k}\right) \right] \times \qquad \text{[Equation 1]}$$
$$w \cdot \mathrm{sinc}\left(\frac{x}{R_0 \lambda} \cdot w\right)$$

Here, x denotes the location of the azimuth, $\psi$ denotes the steering angle, D denotes the aperture of the entire converter, $R_0$ denotes the distance from the center of the converter to the focal point, $\lambda$ denotes the wavelength of ultrasound, and $d_n$ denotes the distance between $n^{th}$ conversion elements from the center of the converter.

Referring to Equation 1, in the case of $x = R_0 \sin\Psi$, the location of the main lobe may be determined, and in the case of $$x = R_0\left(\sin\Psi + \frac{\lambda}{d_k}\right)(k = \pm 1, \pm 2 \ldots ),$$

the location of the grating lobe may be determined.

In the proposed scheme, $d_n$ that determines the location of the grating lobe changes every time by varying locations of the active conversion elements over time. It can be seen that the focal point desired by an operator, namely the location of the main lobe, is disposed in the same area even though $d_n$ changes, but the location of the grating lobe changes with $d_n$. Accordingly, the accumulated influence of the grating lobe can be reduced by changing the location of the grating lobe over time using the proposed scheme. To this end, in the ultrasound therapy device adopting the electrical control scheme according to an embodiment of the present disclosure, the control unit preferably changes the combination of conversion elements that constitute active conversion elements to change the distance between conversion elements from the center of the array type HIFU converter 10 over time.

Figure 5:
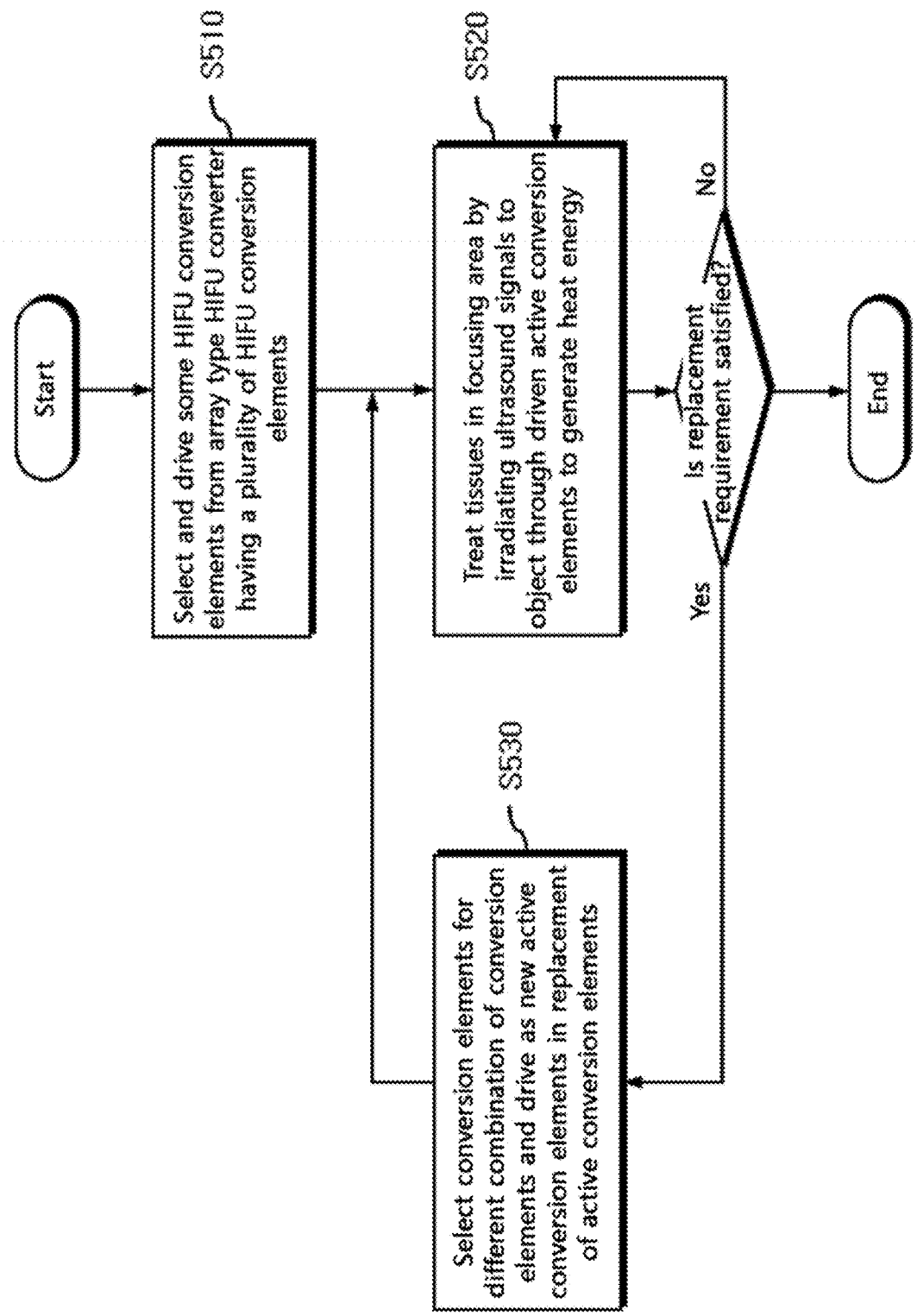
FIG. 5 is a flowchart showing an ultrasound therapy method adopting an electrical control scheme that changes the location of the grating lobe according to an embodiment of the present disclosure.

FIG. 5 is a flowchart showing an ultrasound therapy method adopting the electrical control scheme that changes the location of the grating lobe according to an embodiment of the present disclosure, and the operation of each component of the ultrasound therapy device of FIG. 3 as previously described is reproduced time-sequentially. Accordingly, each step is briefly described to avoid description overlaps.

In S510, some of conversion elements of the array type HIFU converter having a plurality of HIFU conversion elements are selected and driven.

In S520, tissues in a focusing area are treated by irradiating ultrasound signals to an object through the driven active conversion elements to generate heat energy.

Then, inspection is performed to determine whether the replacement requirement of the active conversion elements is satisfied. In the proposed embodiment, it is assumed that a time condition is set as the replacement requirement. When the replacement requirement of the active conversion elements is not satisfied, i.e., a predetermined time period has not passed, the treatment continues in S520.

On the contrary, when a predetermined time period has passed, S530 is performed to select conversion elements for a different combination of conversion elements and drive them as new active conversion elements in replacement of the active conversion elements. Then, S520 enters again to treat the tissues in the focusing area using the driven new active conversion elements.

Additionally, in S530, new active conversion elements are selected by changing the combination of conversion elements that constitute the active conversion elements, the operation of the existing active conversion elements is stopped, and the new active conversion elements are driven. In this instance, beam focusing through the conversion elements included in the combination before the change and beam focusing through the conversion elements included in the combination after the change should be controlled for the same location of the main lobe and different locations of the grating lobe.

Additionally, in S530, it is desirable to change the combination of conversion elements that constitute active conversion elements to change the distance between conversion elements from the center of the array type HIFU converter over time. Further, the active conversion elements selected through S510 and S530 may be selected from conversion elements arranged randomly on the array type HIFU converter, or arranged forming a sparse array, a Fermat's spiral or a concentric ring, or arranged symmetrically with respect to one reference axis (i.e., arranged counter-randomly).

Meanwhile, the ultrasound therapy method adopting the electrical control scheme according to an embodiment of the present disclosure may further include, at the latest before S530, a process of generating and pre-storing a plurality of combinations of conversion elements having the same location of the main lobe and different locations of the grating lobe. In this case, S530 may include reading the pre-stored combinations of conversion elements in a sequential order, and replacing them at a predetermined time interval and drive as active conversion elements.

Figure 6:
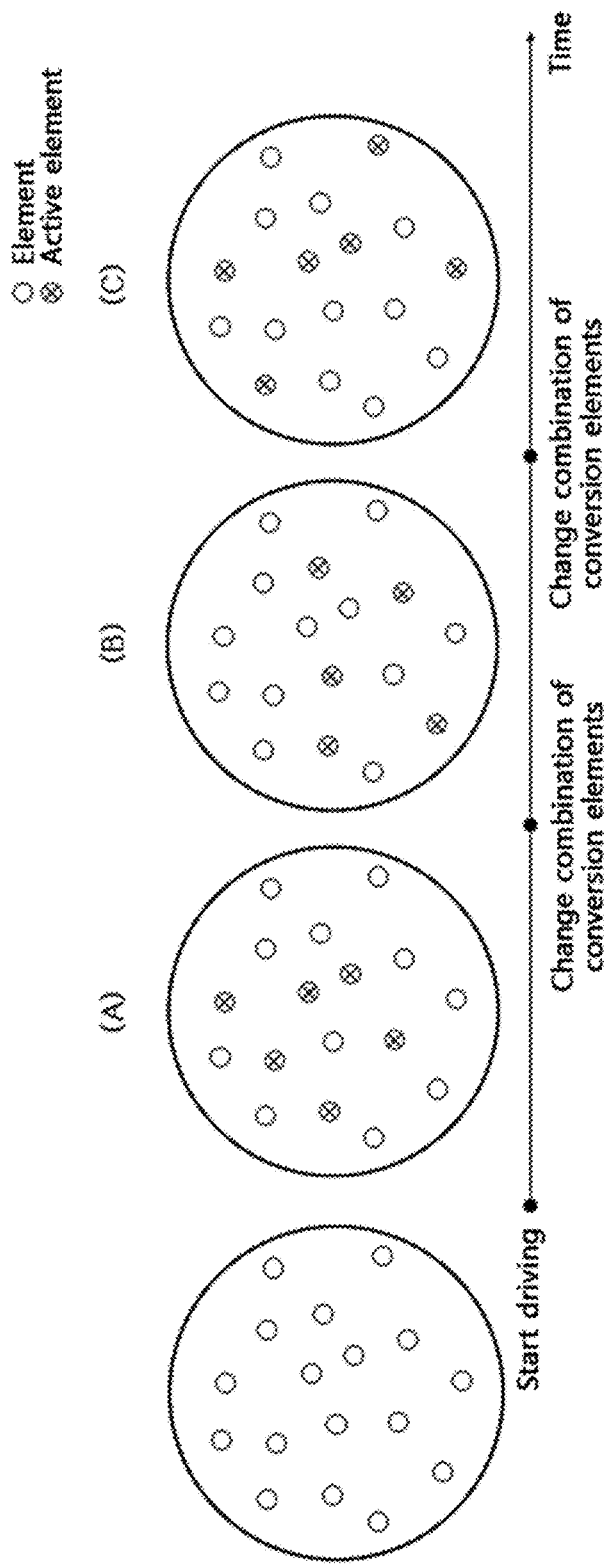
FIG. 6 is an exemplary diagram showing the time-sequential operation of active conversion elements through an electrical control scheme according to an embodiment of the present disclosure.

FIG. 6 is an exemplary diagram showing that active conversion elements are sequentially driven through the electrical control scheme according to an embodiment of the present disclosure, depicting that conversion elements are driven or their combination changes as time goes by.

Referring to FIG. 6, it can be seen that the combination of active conversion elements selected for (A)→(B)→×(C) changes. According to this method, ultrasound radiation is focused on the focusing area by changing the location of the conversion elements activated during ultrasound therapy, and even though the combination of conversion elements changes, the main lobe is controlled to be constantly disposed on the focusing area. In contrast, the selected conversion elements change in location and spacing, and accordingly the area of the grating lobe changes.

Figure 7:
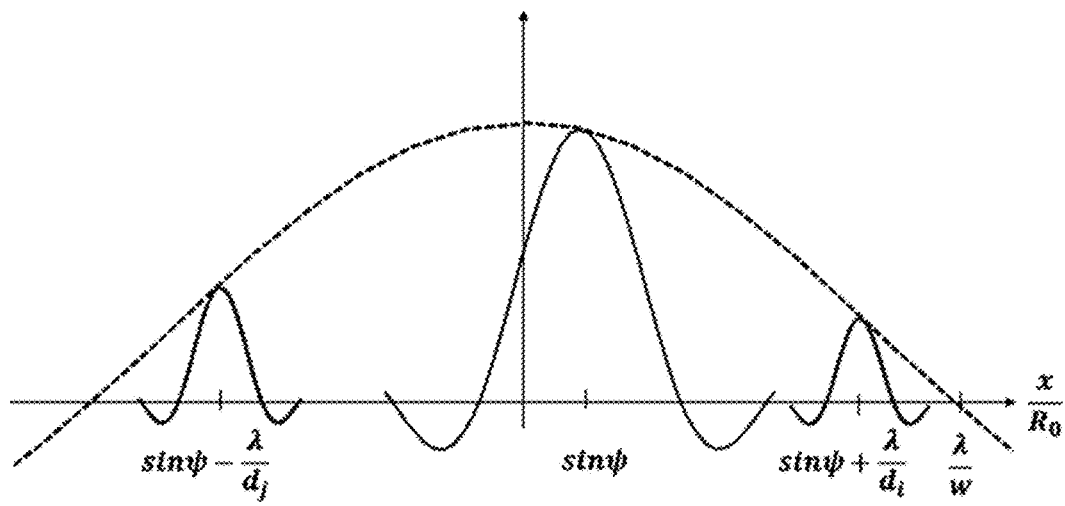
FIG. 7 is an exemplary graph showing a beam pattern generated through an electrical control scheme according to an embodiment of the present disclosure.

FIG. 7 is an exemplary graph showing a beam pattern generated through the electrical control scheme according to an embodiment of the present disclosure. Referring to FIG. 7, as described in the previously-described Equation 1, the main lobe with the highest signal strength is formed at the location of the focal point, $$\frac{x}{R_0} = \sin\psi,$$

and the grating lobe with a lower signal strength than the main lobe is formed at an area other than the focal point, $$\frac{x}{R_0} = \sin\psi + \frac{k}{d_k}(k = \pm 1, \pm 2 \ldots ).$$

In this instance, active conversion elements are constructed with varying distances between conversion elements from the center of the HIFU converter to change the location $d_k$ of the grating lobe, thereby reducing damage in areas other than the focusing spot or the main lobe.

2) Mechanical Control Scheme

Figure 8:
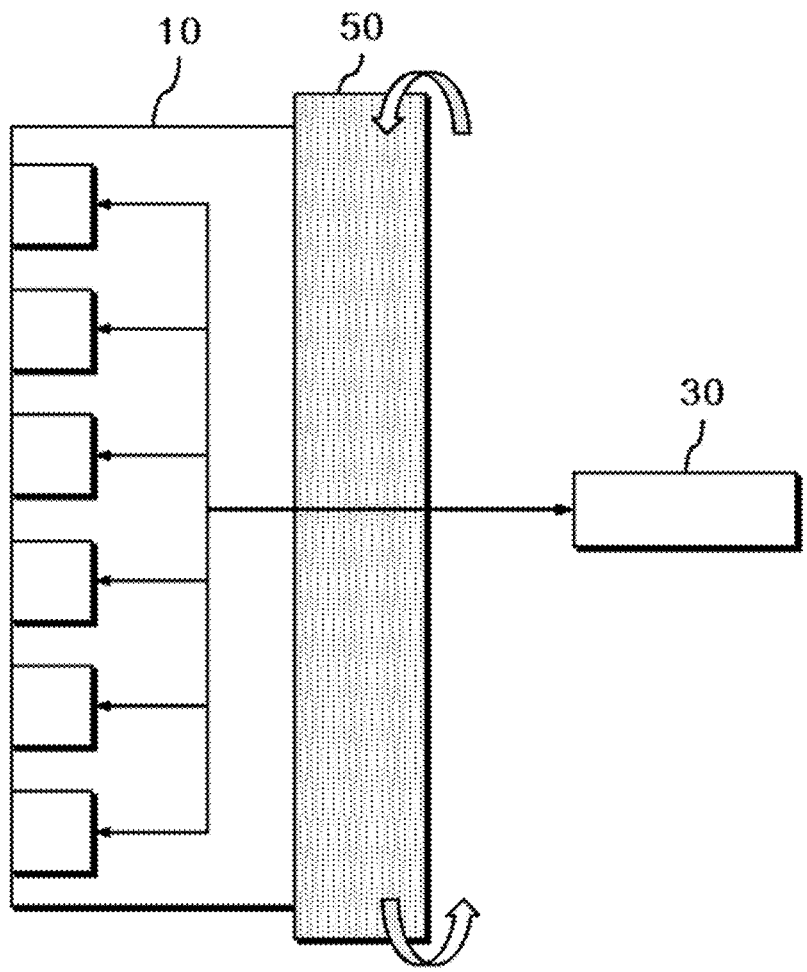
FIG. 8 is a block diagram showing an ultrasound therapy device adopting a mechanical control scheme that changes the location of the grating lobe according to another embodiment of the present disclosure.

FIG. 8 is a block diagram showing the ultrasound therapy device adopting the mechanical control scheme that changes the location of the grating lobe according to another embodiment of the present disclosure.

The array type HIFU converter 10 has a plurality of HIFU conversion elements. In this instance, the array type HIFU converter 10 used in the mechanical control scheme of FIG. 8 has conversion elements disposed on a frame regularly or irregularly, and the total number of conversion elements is preferably equal to or larger than the number of conversion elements activated at one point in time. Among them, when all the conversion elements are simultaneously driven (i.e., all the conversion elements are active conversion elements), system complexity may reduce compared to the electrical control scheme proposed previously through FIG. 3, but a separate means (rotating structure) for changing the location of the grating lobe is necessary.

Meanwhile, the conversion elements may be arranged randomly on the array type HIFU converter 10, may be arranged forming a sparse array, a Fermat's spiral or a concentric ring, or may be arranged symmetrically with respect to one reference axis (i.e., arranged counter-randomly).

The control unit 30 performs control to treat tissues in a focusing area by driving the conversion elements of the array type HIFU converter 10 and irradiating ultrasound signals to an object to generate heat energy. The control unit 30 drives all or some of the conversion elements of the array type HIFU converter 10, and when some conversion elements are driven, it is possible to change the location of the grating lobe more effectively by applying the electrical control scheme which changes the combination of conversion elements that constitute active conversion elements together. That is, the mechanical control scheme and the electrical control scheme may be used together. In this case, control may be performed such that the focusing area formed by beam focusing implemented by the driven conversion elements is disposed on the rotation axis of the rotation unit.

The rotation unit 50 is a means that rotates the array type HIFU converter 10 while maintaining the plane facing the object. The rotation unit 50 rotates the array type HIFU converter 10 around the center of the array type HIFU converter 10, to serve to continuously change the location of the grating lobe over time.

Figure 9:
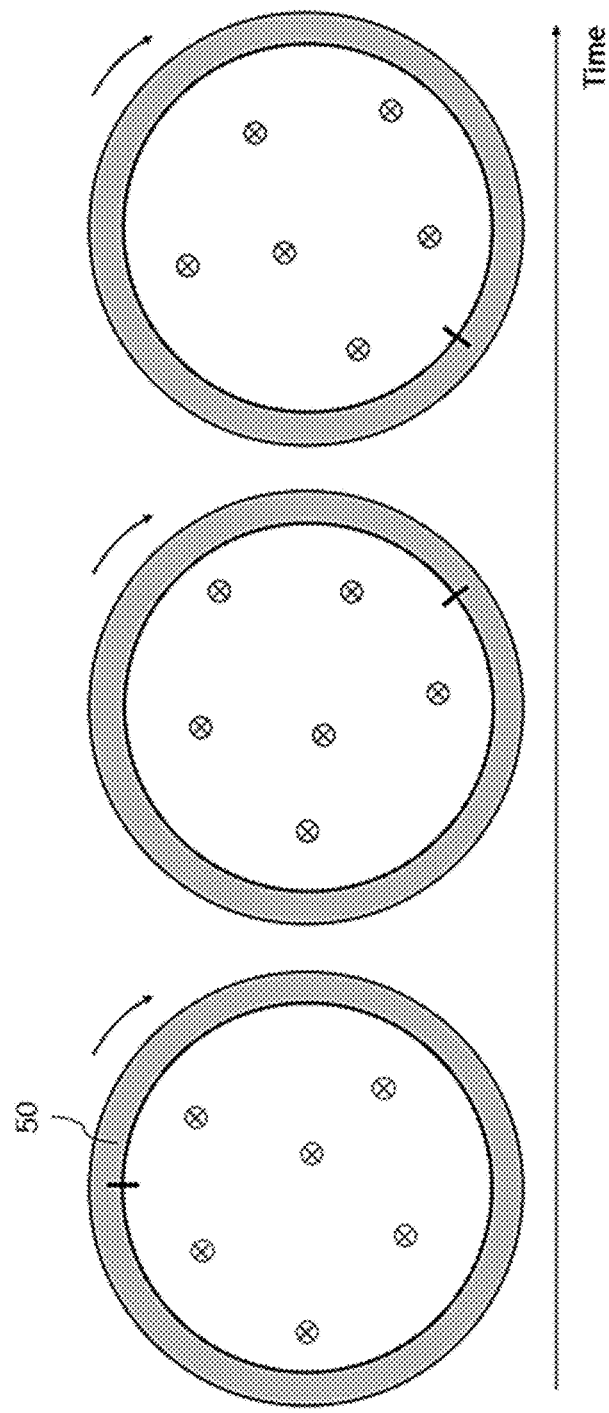
FIG. 9 is an exemplary diagram showing changes in the location of conversion elements over time through a mechanical control scheme according to another embodiment of the present disclosure.

FIG. 9 is an exemplary diagram showing changes in the location of conversion elements over time through the mechanical control scheme according to another embodiment of the present disclosure. Referring to FIG. 9, as time goes by, by rotation of the rotation unit 50 that supports the array type HIFU converter, an effect can be obtained as if the combination of conversion elements of the HIFU converter changes with respect to the object to be treated. That is, there is no change in the active conversion elements driven on the array type HIFU converter, but the location of the grating lobe is changed by rotating the array type HIFU converter itself.

Meanwhile, when performing ultrasound therapy according to the mechanical control scheme using the rotation means, the focusing area or the main lobe formed by beam focusing, and correlation with the rotation axis may be problematic. That is, each of 'on-axis' in which the focusing area is disposed on the rotation axis and 'off-axis' in which the focusing area is not disposed on the rotation axis will be separately described.

The two cases are the same in ultrasound irradiation while rotating the rotation unit 50 that supports the array type HIFU converter as the treatment time continues, but in the case of 'on-axis' focusing area, the same irradiation is performed with no need for separate control of ultrasound irradiation. This is because even though the array type HIFU converter is rotated, the location of the main lobe is equally disposed 'on-axis', and only the location of the grating lobe changes.

On the contrary, in the case of 'off-axis' focusing area, when the array type HIFU converter is rotated without separate control of ultrasound irradiation, the main lobe is disposed in an area other than the focusing area. Accordingly, there is a need to focus ultrasound by continuously controlling the ultrasound irradiation differently to focus ultrasound from the rotated array type HIFU converter to the focusing area. In this instance, in case that the conversion elements disposed in the array type HIFU converter are not regular, when the rotation unit is driven, an effect appears as if there is a change to a different array of conversion elements, and even though ultrasound is focused on the same focusing area, the grating lobe is formed in a different area, so ultrasound therapy may continue without needing to change the combination of active conversion elements.

In summary, when the focusing area formed by beam focusing is disposed on the rotation axis of the rotation unit 50, the control unit may fix the location of the main lobe to the object to be treated without any change in beam focusing signals irrespective of rotation of the array type HIFU converter. On the contrary, when the focusing area formed by beam focusing is not disposed on the rotation axis of the rotation unit 50, the control unit preferably controls the beam focusing signals of each of the conversion elements of the array type HIFU converter such that the main lobe changing in focusing position with the rotation of the array type HIFU converter is disposed in the object to be treated.

Figure 10:
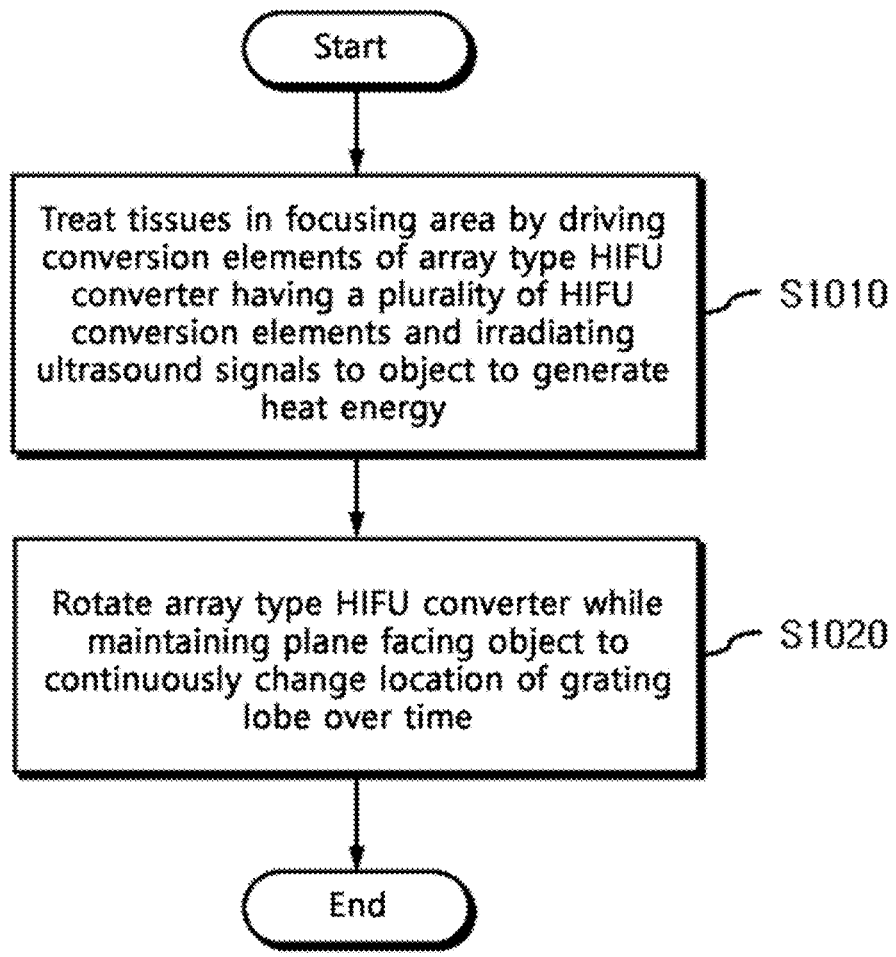
FIGS. 10 and 11 are flowcharts showing an ultrasound therapy method adopting a mechanical control scheme that changes the location of the grating lobe according to another embodiment of the present disclosure.
Figure 11:
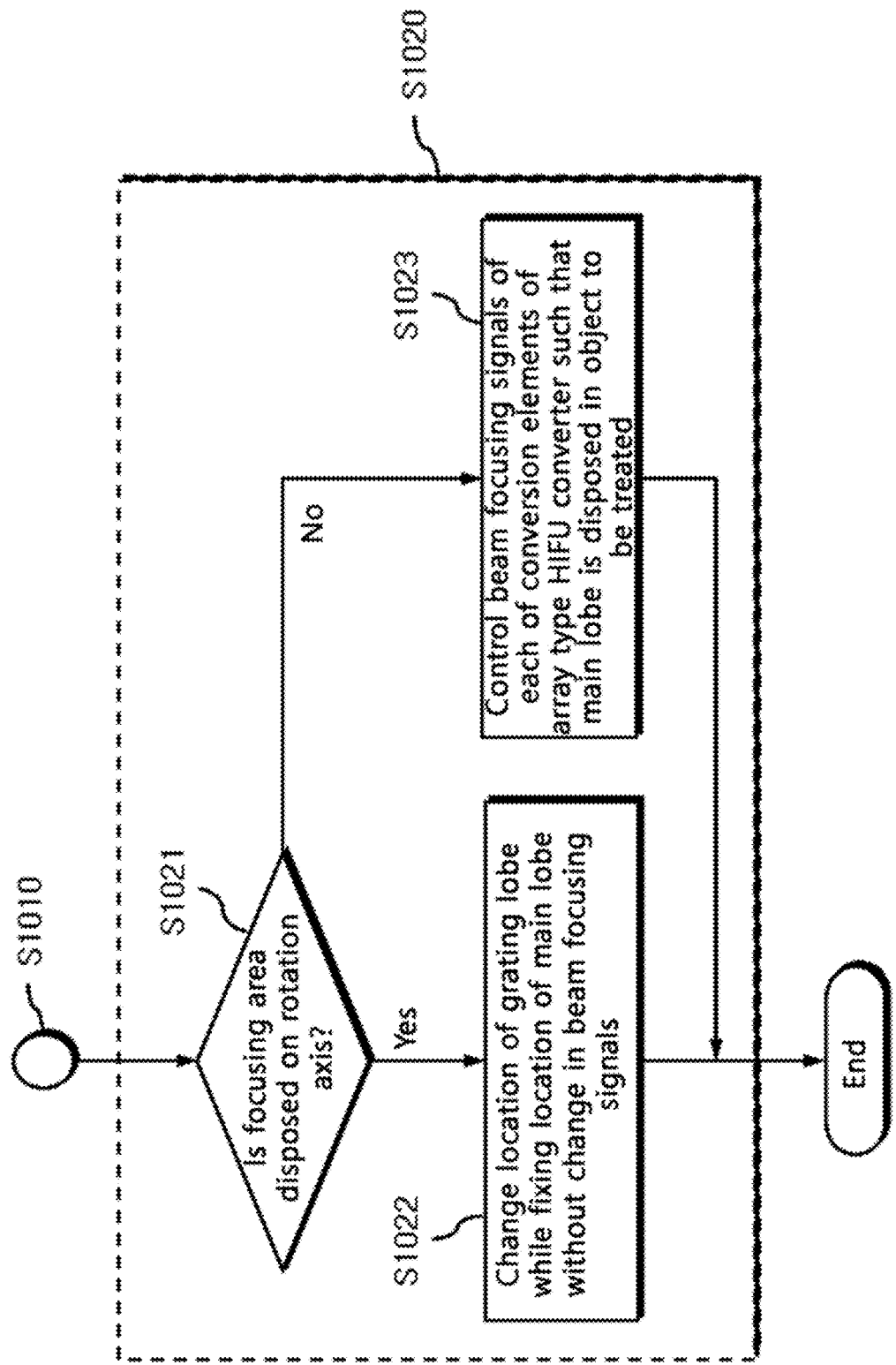

FIGS. 10 and 11 are flowcharts showing the ultrasound therapy method adopting the mechanical control scheme that changes the location of the grating lobe according to another embodiment of the present disclosure, and the operation of each component of the ultrasound therapy device of FIG. 8 as previously described is reproduced time-sequentially. Accordingly, each step is briefly described to avoid description overlaps.

In S1010, tissues in a focusing area are treated by driving conversion elements of the array type HIFU converter having a plurality of HIFU conversion elements and irradiating ultrasound signals to an object to generate heat energy.

In S1020, the array type HIFU converter is rotated while maintaining the plane facing the object, to continuously change the location of the grating lobe over time.

Meanwhile, when some of the conversion elements are driven through S1020, it is possible to change the location of the grating lobe more effectively by applying the electrical control scheme which changes the combination of conversion elements that constitute active conversion elements together. That is, the mechanical control scheme and the electrical control scheme may be used together. In this case, control may be performed such that the focusing area formed by beam focusing implemented by the driven conversion elements is disposed on the rotation axis of the rotation unit.

The sub-operation depending on whether or not the focusing area is disposed on the rotation axis will be described below in more detail with reference to FIG. 11.

First, S1021, inspection is performed to determine whether the focusing area formed by beam focusing is disposed on the rotation axis of the rotation unit.

As a result of inspection, when the focusing area formed by beam focusing is disposed on the rotation axis of the rotation unit, S1022 is performed. In S1022, the location of the main lobe may be fixed to the object to be treated without any change in beam focusing signals irrespective of rotation of the array type HIFU converter.

On the contrary, when the focusing area formed by beam focusing is not disposed on the rotation axis of the rotation unit, S1023 is performed. In S1023, it is desirable to control the beam focusing signals of each of the conversion elements of the array type HIFU converter such that the main lobe changing in focusing position with the rotation of the array type HIFU converter is disposed in the object to be treated.

The present disclosure has been hereinabove described with regard to its various embodiments. Those having ordinary skill in the technical field pertaining to the present disclosure will understand that the present disclosure may be embodied in modified form without departing from the essential feature of the present disclosure. Therefore, the disclosed embodiments should be considered in an illustrative sense, rather than in a limitative sense. The scope of the present disclosure is defined by the appended claims rather than the foregoing description, and it should be interpreted that the present disclosure covers all differences within its equivalent scope.

INDUSTRIAL APPLICABILITY

According to the embodiments of the present disclosure as described above, the electrical control scheme or the mechanical control scheme is adopted to continuously change the location of the grating lobe while fixing the location of the main lobe, thereby suppressing the effect of ultrasound being focused on an unintended area due to the grating lobe, which is one of side effects of the conventional high intensity focused ultrasound (HIFU) treatment, and reducing local heating in normal tissues, and consequently, mitigating pain in patients during treatment and reducing the risk of damage to normal tissues. Additionally, there was a risk for burns to skin in contact with the converter in the course of treatment, but because the converter increasing in temperature during treatment continuously changes in location, this risk for burns can be reduced. In addition, it is possible to reduce the time spent in the cooling process for cooling down the heat generated during treatment, and accordingly reduce the entire treatment time, and enable more stable and efficient ultrasound therapy.

The invention claimed is:

1. An ultrasound therapy device, comprising:
    an array type high intensity focused ultrasound (HIFU) converter having a plurality of HIFU conversion elements; and
    a control unit which performs control to treat tissues in a focusing area by selecting and driving some of the plurality of HIFU conversion elements of the array type HIFU converter and irradiating ultrasound signals to an object by driving the some of the plurality of HIFU conversion elements as driven active HIFU conversion elements to generate heat energy, wherein,
    after an elapse of a predetermined time period, the control unit drives other of the plurality of HIFU conversion elements selected for a different combination of HIFU conversion elements as new active HIFU conversion elements in replacement of the driven active HIFU conversion elements,
    the control unit changes a combination of HIFU conversion elements that constitute the driven active HIFU conversion elements over time, and
    beam focusing through the HIFU conversion elements included in the driven active HIFU conversion elements before the change and beam focusing through the new active HIFU conversion elements after the change have a same location of a main lobe and a different location of a grating lobe.

2. The ultrasound therapy device according to claim 1, further comprising:
    a storage unit which generates and pre-stores a plurality of combinations of HIFU conversion elements having the same location of the main lobe and the different location of the grating lobe,
    wherein the control unit reads the combinations of HIFU conversion elements stored in the storage unit in a sequential order, and makes replacement and drives as the new active HIFU conversion elements at the predetermined time period.

3. The ultrasound therapy device according to claim 1, wherein the control unit changes a combination of HIFU conversion elements that constitute the driven active HIFU conversion elements for varying distances between the plurality of HIFU conversion elements from a center of the array type HIFU converter over time.

4. The ultrasound therapy device according to claim 1, wherein the driven active HIFU conversion elements are selected from the plurality of HIFU conversion elements arranged randomly on the array type HIFU converter, or arranged forming a sparse array, a Fermat's spiral or a concentric ring, or arranged symmetrically with respect to one reference axis.

5. An ultrasound therapy method, comprising:
    (a) selecting and driving some HIFU conversion elements as active HIFU conversion elements from an array type high intensity focused ultrasound (HIFU) converter having a plurality of HIFU conversion elements;
    (b) treating tissues in a focusing area by irradiating ultrasound signals to an object through the driven active HIFU conversion elements to generate heat energy;
    (c) after an elapse of a predetermined time period, selecting others of the plurality of HIFU conversion elements for a different combination of HIFU conversion elements and driving as new active HIFU conversion elements in replacement of the driven active HIFU conversion elements; and
    (d) treating the tissues in the focusing area using the new active HIFU conversion elements, wherein
    the step (c) includes:
        selecting the new active HIFU conversion elements by changing a combination of the plurality of HIFU conversion elements that constitute the new active HIFU conversion elements; and
        stopping driving of the driven active HIFU conversion elements, and driving the new active HIFU conversion elements, and
    beam focusing through the driven active HIFU conversion elements before the change and beam focusing through the new active HIFU conversion elements after the change have a same location of a main lobe and a different location of a grating lobe.

6. The ultrasound therapy method according to claim 5, further comprising:
    generating and pre-storing a plurality of combinations of the plurality of HIFU conversion elements having the same location of the main lobe and the different location of the grating lobe,
    wherein the step (c) further includes reading the pre-stored plurality of combinations of the plurality of HIFU conversion elements in a sequential order and making replacement and driving as the new active HIFU conversion elements at the predetermined time period.

7. The ultrasound therapy method according to claim 5, wherein the step (c) further includes changing a combination of the active HIFU conversion elements for varying distances between the plurality of HIFU conversion elements from a center of the array type HIFU converter over time.

8. The ultrasound therapy method according to claim 5, wherein the active HIFU conversion elements selected through the step (a) and the new active HIFU conversion elements selected through the step (c) are selected from the plurality of HIFU conversion elements arranged randomly on the array type HIFU converter, or arranged forming a sparse array, a Fermat's spiral or a concentric ring, or arranged symmetrically with respect to one reference axis.

* * * * *